United States Patent
Nakano et al.

[11] Patent Number: 6,117,447
[45] Date of Patent: Sep. 12, 2000

[54] PERCUTANEOUS ABSORPTION TYPE PREPARATION

[75] Inventors: Yoshihisa Nakano; Mitsuhiko Hori; Keiji Yamamoto; Saburo Otsuka, all of Ibaraki, Japan

[73] Assignees: Nitto Denko-Corporation, Osaka; Hokuriku Seiyaku Co., Ltd., Fukui, both of Japan

[21] Appl. No.: 09/203,749

[22] Filed: Dec. 2, 1998

[30] Foreign Application Priority Data

Dec. 12, 1997 [JP] Japan ................................. 9-342582
Oct. 26, 1998 [JP] Japan ................................ 10-304498

[51] Int. Cl.$^7$ ..................................................... A61K 9/70
[52] U.S. Cl. ........................ 424/448; 424/449; 514/947; 514/946
[58] Field of Search .................................. 424/448, 449; 514/947, 946

[56] References Cited

U.S. PATENT DOCUMENTS

| | | | |
|---|---|---|---|
| 5,254,348 | 10/1993 | Hoffmann et al. | 424/449 |
| 5,300,291 | 4/1994 | Sablotsky et al. | 424/78.18 |
| 5,312,627 | 5/1994 | Stroppolo et al. | 424/448 |
| 5,571,530 | 11/1996 | Nakano et al. | 424/448 |
| 5,639,472 | 6/1997 | Yamamoto et al. | 424/449 |
| 5,683,710 | 11/1997 | Akemi et al. | 424/448 |

FOREIGN PATENT DOCUMENTS

| | | |
|---|---|---|
| 0 374 980 A2 | 6/1990 | European Pat. Off. . |
| 0 439 180 A2 | 7/1991 | European Pat. Off. . |
| 0 523 537 A1 | 1/1993 | European Pat. Off. . |
| 0 677 290 A1 | 10/1995 | European Pat. Off. . |

OTHER PUBLICATIONS

Chemical Abstracts, vol. 126, No. 8, Feb. 24, 1997, XP–002116852.

*Primary Examiner*—Gollamudi S. Kishore
*Assistant Examiner*—Liliana Di Nola-Baron
*Attorney, Agent, or Firm*—Sughrue, Mion, Zinn, Macpeak & Seas, PLLC

[57] ABSTRACT

A percutaneous absorption type preparation comprising a support and a plaster layer laminated thereon, which composes tulobuterol in a proportion of not less than 5 wt % in a dissolution state and an adhesive. The preparation of the present invention retains the active ingredient, tulobuterol, at a high concentration in a complete dissolution state in the plaster layer. Therefore, it is free of time-course changes in drug releasing property and adhesive property caused by precipitation of drug crystals with the lapse of time. The inventive preparation is superior in percutaneous absorption of the drug, particularly percutaneous absorption rate at the initial stage of the administration; shows superior duration of efficacy by maintaining effective blood concentration for a long time; and is associated with less changes with the lapse of time in adhesive property such as adhesion to the skin.

5 Claims, 1 Drawing Sheet

PERCUTANEOUS ABSORPTION TYPE PREPARATION

TECHNICAL FIELD OF THE INVENTION

The present invention relates to a percutaneous absorption type preparation for continuous administration of tulobuterol through the skin into the body upon application thereof to the skin surface. More particularly, the present invention relates to a percutaneous absorption type preparation superior in adhesion to the skin, superior in initial absorption property of tulobuterol and capable of sustaining an effective concentration of tulobuterol in blood, upon application of the preparation to the skin surface.

BACKGROUND OF THE INVENTION

Tulobuterol has a bronchodilating action by selectively stimulating $\beta_2$ receptor of the sympathetic nerve. Thus, it has been widely used for treating chronic bronchitis, bronchial asthma and the like in an attempt to reduce dyspnea of patients with respiratory tract stricture.

Tulobuterol is generally administered into the body by oral administration using, for example, tablets and the like. This method, however, is associated with the problems of difficulty confronted in administering to infants and the like, emergence of side effects caused by a steep increase in blood concentration of the drug, short duration of drug effect, and the like. To solve these problems, there have been developed percutaneous absorption type preparations containing various drugs to administer the drug into the body through the skin surface. With respect to tulobuterol, Japanese Patent Unexamined Publication No. 5-194202 (LTS Lohmann Therapie Systeme), Japanese Patent Unexamined Publication No. 5-238953 (Zambon Group S.p.A), Japanese Patent Unexamined Publication No. 7-285854 (Nitto Denko Corporation) and Japanese Patent Examined Publication No. 7-25669 (Nitto Denko Corporation) propose percutaneous absorption type preparations thereof.

These publications mostly relate to a preparation containing tulobuterol in a plaster layer in a concentration of not less than solubility of the drug in an adhesive, wherein tulobuterol is partially dispersed in the plaster layer in a crystalline state. In general, a higher concentration of a drug dissolved in a plaster layer is considered to lead to a higher percutaneous absorption rate of the drug, and a higher content of a drug in a plaster layer is considered to lead to a longer duration of drug release. However, keeping a drug in a dissolution state at a high concentration stably in a polymer used to form a plaster layer is generally difficult to achieve. For satisfactory percutaneous absorption rate and sustained release of a drug, therefore, the drug is contained in a plaster layer at a high concentration of not less than the solubility of the drug in an adhesive and part of the drug is present in a crystalline state in the plaster layer, as disclosed in the above-mentioned prior art publications.

A preparation containing solid drug crystals in the plaster layer is susceptible to precipitation of the drug crystals on the surface of the plaster layer where it comes into contact with the skin, thus degrading the adhesive property to the skin. Inasmuch as the diffusion rate of the drug molecule in the polymer is strikingly slower than that in a liquid, the drug crystals do not precipitate quickly in the plaster layer. Gradual crystallization of the drug in the plaster layer is expected to influence the adhesive property of the preparation to the skin and drug releasing property with the lapse of time. When the drug is contained at a concentration of not less than the solubility thereof in the adhesive, the preparation containing part of the drug in a crystalline state in the plaster layer may fail to provide sufficient stability of the preparation quality. This poses a high threshold in achieving superior percutaneous absorption, long duration of the efficacy and superior adhesion to the skin, of the preparation.

SUMMARY OF THE INVENTION

In view of the above, the present invention now provides a percutaneous absorption type preparation containing tulobuterol dissolved in a plaster layer at a high concentration of not less than 5 wt %.

Thus, the present invention provides the following.

(1) A percutaneous absorption type preparation comprising a support and a plaster layer laminated thereon, said plaster layer comprising tulobuterol in a proportion of not less than 5 wt % in a dissolution state and an adhesive.

(2) The percutaneous absorption type preparation of (1) above, wherein the adhesive is an acrylic adhesive or a rubber adhesive.

(3) The percutaneous absorption type preparation of (2) above, wherein the acrylic adhesive comprises a polymer comprising an alkyl (meth)acrylate, wherein the alkyl group has 4 to 12 carbon atoms, in a proportion of not less than 50 wt %.

(4) The percutaneous absorption type preparation of (2) above, wherein the acrylic adhesive comprises a copolymer comprising an alkyl (meth)acrylate, wherein the alkyl group has 4 to 12 carbon atoms, in a proportion of not less than 60 to 98 wt %, and a functional monomer having at least one unsaturated double bond in a molecule and a functional group on a side chain, in a proportion of 2 to 40 wt %.

(5) The percutaneous absorption type preparation of (4) above, wherein the functional group of the functional monomer is a member selected from the group consisting of carboxyl group, hydroxyl group, sulfonic acid group, amino group, amido group, alkoxyl group, cyano group and acyloxy group.

(6) The percutaneous absorption type preparation of (4) above, wherein the functional monomer is a member selected from the group consisting of (meth)acrylic acid, 2-hydroxyethyl (meth)acrylate, styrenesulfonic acid, (meth)acrylamide, vinyl pyrrolidone, 2-aminoethyl (meth)acrylate, acrylonitrile, 2-methoxyethyl (meth)acrylate and vinyl acetate.

(7) The percutaneous absorption type preparation of (2) above, wherein the rubber adhesive comprises at least one polymer selected from the group consisting of polyisobutylene and a styrene-diene-styrene block copolymer.

(8) The percutaneous absorption type preparation of any of (1) to (7) above, wherein the plaster layer further comprises at least one additive selected from the group consisting of an ester of a fatty acid having 12 to 16 carbon atoms, monoglyceride of a fatty acid having 8 to 10 carbon atoms, an ester of a dibasic acid having 6 to 10 carbon atoms, a polyoxyethylene alkyl ether having an addition molar number of oxyethylene of 2 to 5, and a polyoxyethylene alkylphenyl ether having an addition molar number of oxyethylene of 2 to 5, in a proportion of 5 to 50 wt %.

DETAILED DESCRIPTION OF THE INVENTION

Figure 1:
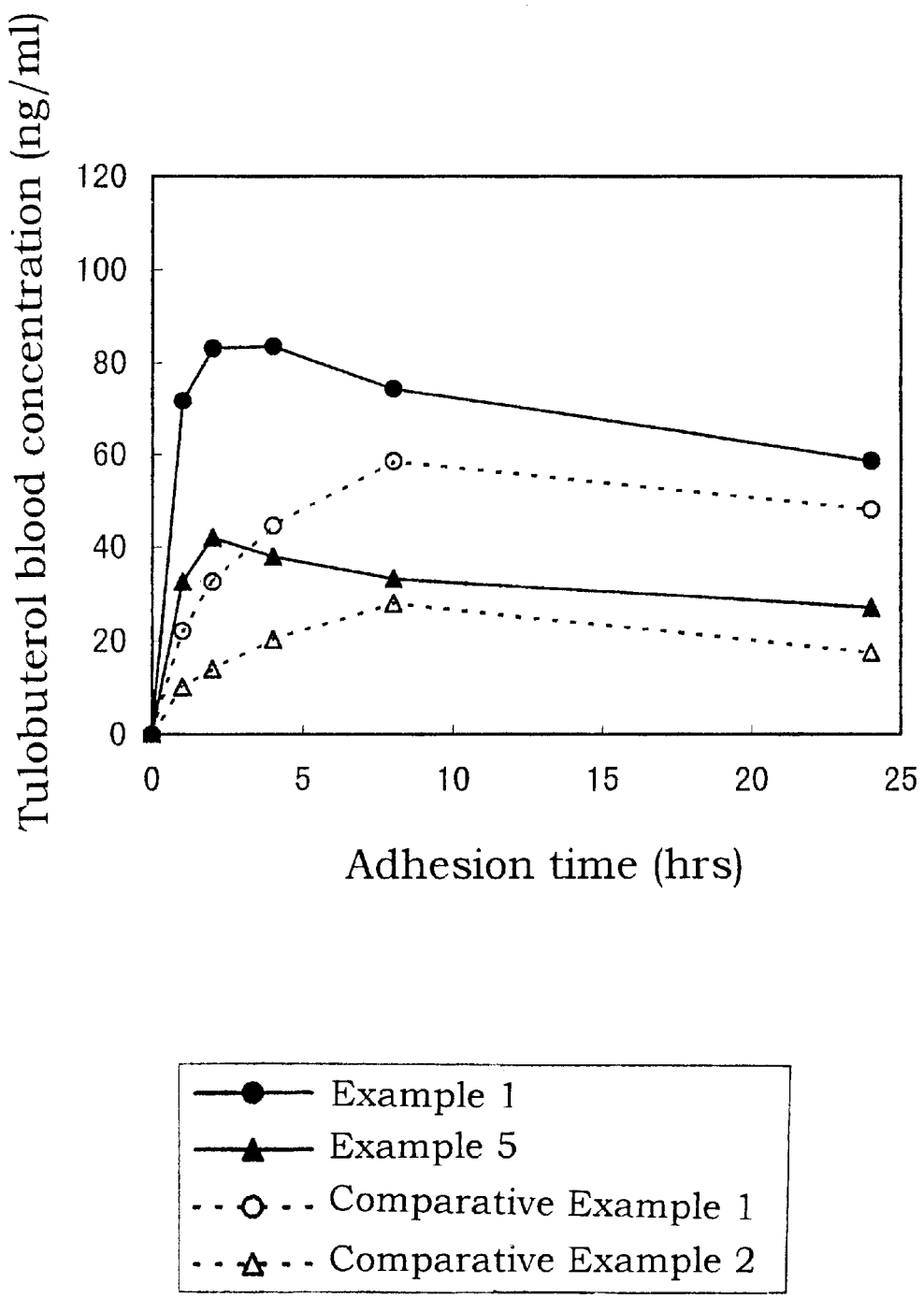
FIG. 1 is a graph showing time-course changes of tulobuterol blood concentration in Experimental Example 3.

The percutaneous absorption type preparation of the present invention contains tulobuterol at a high concentration in a dissolution state in a plaster layer. The percutaneous absorption type preparation of the present invention is free of precipitation of drug crystals even at high concentrations. It contains tulobuterol in a complete dissolution state in a plaster layer, as a result of which the preparation shows superior percutaneous absorption of the drug, particularly superior percutaneous absorption rate at the initial stage of administration, superior duration of the efficacy, which is attributable to a long-time maintenance of effective blood concentration, and reduced time-course changes of adhesive property such as adhesion to the skin.

Tulobuterol to be contained in the percutaneous absorption type preparation of the present invention is dissolved in the adhesive in the plaster layer and should be present in a dissolution state. When tulobuterol in the plaster layer is in a crystalline state, it precipitates as crystals with the lapse of time. This in turn undesirably changes adhesive property to the skin, percutaneous absorption property and drug releasing property, of the preparation with the lapse of time.

As used herein, the presence of tulobuterol in a dissolution state means that crystals of tulobuterol are not visually or microscopically observed in the plaster layer so that the plaster layer is uniform.

Conventional preparation containing tulobuterol in a dissolution state in a plaster layer could achieve only a concentration of not more than 3 wt %, and the present invention is the first to achieve a preparation containing tulobuterol in a dissolution state in a concentration of not less than 5 wt %, preferably not less than 10 wt %.

In the present invention, the concentration of tulobuterol need only be not less than 5 wt % in the plaster layer to achieve the desired effect.

The adhesive to be contained in the plaster layer is subject to no particular limitation as long as it can dissolve tulobuterol in the plaster layer and the solubility thereof reaches not less than 5 wt %. For better adhesion to the skin, acrylic adhesive and rubber adhesive are particularly preferable.

The above-mentioned acrylic adhesive comprises an acrylic polymer which is exemplified by polymers and copolymers obtained by polymerization of alkyl (meth) acrylate. The alkyl of alkyl (meth)acrylate here is preferably a linear or branched alkyl having 4 to 12 carbon atoms. Examples of said alkyl (meth)acrylate include butyl (meth) acrylate, t-butyl (meth)acrylate, pentyl (meth)acrylate, hexyl (meth)acrylate, heptyl (meth)acrylate, octyl (meth)acrylate, isooctyl (meth)acrylate, nonyl (meth)acrylate, isononyl (meth)acrylate, decyl (meth)acrylate, undecyl (meth) acrylate, dodecyl (meth)acrylate, 2-ethylhexyl (meth) acrylate and the like. This alkyl (meth)acrylate is preferably polymerized in a proportion of not less than 50 wt %, more preferably not less than 60 wt %.

The acrylic polymer to be used in the present invention may be a copolymer obtained by copolymerizing the aforesaid alkyl (meth)acrylate and one or more monomers from the following monomers.

Said monomer is exemplified by functional monomers having at least one unsaturated double bond in a molecule and a functional group, such as carboxyl group, hydroxyl group, sulfonic acid group, amino group, amido group, alkoxyl group, cyano group, acyloxy group and the like, on the side chain. Specific examples thereof include alkoxy-modified alkyl (meth)acrylate monomers wherein the alkyl group of alkyl (meth)acrylate has been modified with a linear or branched alkoxy having 1 to 4 carbon atoms (e.g., methoxy, ethoxy and the like), such as 2-methoxyethyl (meth)acrylate and 2-ethoxyethyl (meth)acrylate; acrylonitrile; vinyl acetate; vinyl propionate; vinyl pyrrolidone; vinyl caprolactam; (meth)acrylic acid; 2-hydroxyethyl (meth)acrylate; styrenesulfonic acid; (meth)acrylamide; 2-aminoethyl (meth)acrylate; and the like.

When a copolymer obtained by copolymerizing an alkyl (meth)acrylate and the above-mentioned functional monomer is used as this acrylic polymer, alkyl (meth)acrylate (60 to 98 wt % preferably 65 to 97 wt %) and the monomer (2 to 40 wt %, preferably 3 to 35 wt %) are preferably copolymerized.

Examples of the rubber adhesive include polyisobutylene-polybutene adhesive, styrenediene-styrene block copolymer, styrene-butadiene adhesive, nitrile adhesive, chloroplene adhesive, vinyl pyridine adhesive, polyisobutylene adhesive, butyl adhesive, isoprene-isobutylene adhesive and the like. Of these, polyisobutylene and styrene-diene-styrene block copolymer (e.g., styrene-butadiene-styrene block copolymer (SBS), styrene-isoprene-styrene block copolymer (SIS) and the like) are preferably used in consideration of solubility of tulobuterol and adhesion to the skin. These may be used in combination.

The rubber adhesive may be a mixture of ingredients having the same or different components and having different average molecular weights to achieve adequate adhesive property and drug solubility. Taking polyisobutylene for example, a mixture of polyisobutylene having a high average molecular weight of 300,000 to 2,500,000, polyisobutylene having a medium average molecular weight of 10,000 to 200,000 and/or polyisobutylene having a low average molecular weight of 500 to 4,000, is preferable. In this case, a high molecular weight polyisobutylene (10 to 80 wt %, preferably 20 to 50 wt %), a medium molecular weight polyisobutylene (0 to 90 wt %, preferably 10 to 80 wt %) and a low molecular weight polyisobutylene (0 to 80 wt %, preferably 10 to 60 wt %) are preferably mixed.

By the average molecular weight is meant in the present invention a viscosity average molecular weight calculated from the viscosity formula of Flory.

This rubber adhesive may contain a tackifier such as rosin resin, polyterpene resin, chroman-indene resin, petroleum resin, terpene-phenol resin, xylene resin and the like, for appropriate adhesive property. One or more kinds of the tackifiers may be added to the rubber adhesive in a proportion of not more than 50 wt %, preferably 5 to 40 wt %, of the rubber adhesive.

In the present invention, a solubilizer can be added to the plaster layer, so that tulobuterol therein has a higher solubility in a plaster layer, and high concentration tulobuterol can be kept in complete dissolution. The additive to be added for this end may be any as long as it shows superior compatibility (miscibility) with the adhesive, dissolves tulobuterol sufficiently, does not cause separation of the additive from the adhesive component with the lapse of time, and does not exert adverse influence on adhesive property and release property. For example, at least one member selected from an ester of a fatty acid having 12 to 16 carbon atoms, monoglyceride of a fatty acid having 8 to 10 carbon atoms, an ester of a dibasic acid having 6 to 10 carbon atoms, a polyoxyethylene alkyl ether having an addition molar number of oxyethylene of 2 to 5, and a polyoxyethylene alkylphenyl ether having an addition molar number of oxyethylene of 2 to 5, the latter two being nonionic surfactants, can be used.

Examples of the above-mentioned ester of a fatty acid having 12 to 16 carbon atoms include $C_1$ to $C_{10}$ alkyl esters of $C_{12}$ to $C_{16}$ fatty acid, such as hexyl laurate ($C_{12}$), isopropyl myristate ($C_{14}$), isopropyl palmitate ($C_{16}$) and the like.

Examples of the above-mentioned monoglyceride of a fatty acid having 8 to 10 carbon atoms include glycerin monocaprylate ($C_8$), glycerin monocaprate ($C_{10}$) and the like.

Examples of the above-mentioned ester of a dibasic acid having 6 to 10 carbon atoms include $C_1$ to $C_{10}$ alkyl esters of $C_6$ to $C_{10}$ dibasic acid, such as diisopropyl adipate ($C_6$), dioctyl adipate, diethyl sebacate ($C_{10}$) and the like.

In the above-mentioned polyoxyethylene alkyl ether having an addition molar number of oxyethylene of 2 to 5, and polyoxyethylene alkylphenyl ether having an addition molar number of oxyethylene of 2 to 5, the alkyl group has 6 to 18, preferably 8 to 12, carbon atoms. Examples of polyoxyethylene allyl ether include polyoxyethylene lauryl ether, polyoxyethylene alkyl ether, polyoxyethylene cetyl ether and the like. Examples of polyoxyethylene alkylphenyl ether include polyoxyethylene nonylphenyl ether, polyoxyethylene octylphenyl ether and the like.

Of these, isopropyl myristate, which is an ester of a fatty acid having 12 to 16 carbon atoms, glycerin monocaprylate, which is a monoglyceride of a fatty acid having 8 to 10 carbon atoms, diisopropyl adipate, which is an ester of a dibasic acid having 6 to 10 carbon atoms, and a polyoxyethylene octylphenyl ether having an addition molar number of oxyethylene of 2 to 5, which is a polyoxyethylene alkylphenyl ether having an addition molar number of oxyethylene of 2 to 5, are preferable. Particularly preferred is isopropyl myristate.

Said additive is preferably contained in the plaster layer in a proportion of 5 to 50 wt %, preferably 10 to 40 wt %, and more preferably 20 to 40 wt %. When the amount of the additive is less than 5 wt %, higher concentration tulobuterol may not be present in a completely dissolved state in the plaster layer, whereas when it exceeds 50 wt %, cohesive force of the plaster layer may decrease, resulting in frequent remainder of adhesive on the skin surface upon peeling off.

When the aforementioned additives are added to the adhesive having a crosslinking functional group, a crosslinking treatment is desired by the use of a suitable crosslinking means. By the crosslinking treatment, the adhesive assumes a so-called gel state and outflow of additives therein can be suppressed. In addition, a suitable cohesive power can be imparted to the plaster layer. The crosslinking reaction may be carried out by physical crosslinking using ultraviolet irradiation and electron beam irradiation, chemical crosslinking treatment using a crosslinking agent, such as polyisocyanate compound, organic peroxide compound, organic metal salt, metal alcoholate, metal chelate compound, multifunctional compound and the like, or other method.

The thickness of the plaster layer containing the aforementioned adhesive and tulobuterol is preferably 20 to 100 $\mu$m, more preferably 20 to 50 $\mu$m, so that it can stand adhesion to the skin for a long time and reduce remainder of the adhesive on the skin upon peeling off of the preparation.

The support to be used for the percutaneous absorption type preparation in the present invention is not particularly limited as long as it can form and support the plaster layer containing tulobuterol, which is formed on one surface thereof, but a material through which tulobuterol does not substantially permeate, and which particularly has flexibility that enables the preparation to follow curves and movements of skin surface to the extent that no remarkable uncomfortability is felt upon application to the skin surface, is preferable.

Specific examples thereof include monolayer films, such as polyethylene, polypropylene, polyester, poly(vinyl acetate), ethylene/vinyl acetate copolymers, polyvinyl chloride), polyurethane plastic films, metal films (e.g., aluminum foil and tin foil), nonwoven fabric, woven fabric, paper and the like, and laminate films made from these.

The thickness of the support is generally 5 to 500 $\mu$m, preferably 5 to 200 $\mu$m.

The surface of the support, on which the plaster layer is laminated, preferably undergoes a corona discharge treatment, a plasma treatment, an oxidation treatment and the like for an improved adhesion to the plaster layer and an improved anchor effect.

The production method of the percutaneous absorption type preparation of the present invention is not particularly limited. For example, tulobuterol and the adhesive are completely dissolved in an organic solvent, such as ethyl acetate, hexane, toluene and the like, and the obtained solution is cast onto one surface of the support and dried to form a plaster layer on the support. The above-mentioned solution may be cast onto a release liner as a protection film, and dried to form a plaster layer on the release liner, followed by adhesion of the support to the plaster layer, whereby the preparation can be produced.

The exposed surface of the plaster layer of the percutaneous absorption type preparation of the present invention is preferably covered and protected with a release liner until immediately prior to the adhesion to the skin, for the prevention of unnecessary contact of the plaster layer to tools, pouches and the like during production, transport and storage, as well as for the prevention of the degradation of the preparation. When in use, the liner is removed to expose the surface of the plaster layer and the preparation is adhered to the skin for administration.

The release liner is not particularly limited as long as it can be removed easily from the plaster layer when in use, and exemplified by films of polyester, poly(vinyl chloride), poly(vinylidene chloride), polyethylene terephthalate and the like, paper (e.g., woodfree paper and glassine paper), a laminate film of woodfree paper or glassine paper and polyolefin, and the like. They are preferably subjected to a release treatment comprising application of silicone resin, fluororesin and the like on the surface thereof that comes in direct contact with the plaster layer.

The thickness of the release liner is generally 12 to 200 $\mu$m, preferably 50 to 100 $\mu$m.

While the dose of the percutaneous absorption type preparation of the present invention varies depending on the age, body weight, symptom and the like of patient, the administration is usually performed by the application of a preparation containing tulobuterol in an amount of 0.1 –5 mg/patch, to 1–50 $cm^2$ area of the skin of an adult once a day or once every other day.

The present invention is described in more detail by way of Examples and Experimental Examples, to which the invention is not limited. In the following description, "parts" and "%" mean "parts by weight" and "wt %," respectively.

EXAMPLE 1

2-Ethylhexyl acrylate (50 parts), 2-methoxyethyl acrylate (25 parts) and vinyl acetate (25 parts) were polymerized in ethyl acetate under an inert gas atmosphere to give an acrylic adhesive solution. To this solution was added tulobuterol so that its content in the plaster layer was 10%, and the mixture was stirred well. This solution was cast onto a release liner so that the thickness after drying became 40 μm, and dried to give a plaster layer. This plaster layer was adhered to a support (12 μm thick polyester film) to give a percutaneous absorption type preparation of the present invention.

EXAMPLE 2

To the acrylic adhesive solution obtained in Example 1 were added tulobuterol and polyoxyethylene octylphenyl ether (addition molar number of oxyethylene being 3, OP-3, manufactured by NIKKO Chemicals CO. LTD.) as an additive so that their content in the plaster layer was 10% each. The mixture was stirred well and, in the same manner as in Example 1, the percutaneous absorption type preparation of the present invention was obtained.

EXAMPLE 3

2-Ethylhexyl acrylate (95 parts) and acrylic acid (5 parts) were polymerized in ethyl acetate under an inert gas atmosphere to give an acrylic adhesive solution. To this solution was added tulobuterol and isopropyl myristate as an additive so that their contents in the plaster layer were 20% and 30%, respectively, and the mixture was stirred well. As a crosslinking agent, a polyisocyanate compound (trademark CORONATE HL, manufactured by NIPPON POLYURETHANE INDUSTRY CO., LTD.) was added in a proportion of 0.15% of the acrylic adhesive, and the mixture was stirred thoroughly. This solution was cast onto a release liner so that the thickness after drying became 60 μm, and dried to give a plaster layer. Then, the plaster layer was adhered to a support [laminate film of a polyester nonwoven fabric (basic weight 12 g/m$^2$) and 6 μm thick polyester film] on the nonwoven fabric side to give a percutaneous absorption type preparation of the present invention.

For an accelerated crosslinking reaction, the preparation after adhesion to the support was heated at 70° C. for 60 hours.

EXAMPLE 4

To the acrylic adhesive solution obtained in Example 3 were added tulobuterol, and isopropyl myristate and glycerin monocaprylate as additives so that their contents in the plaster layer were 10%, 40% and 5%, respectively. The mixture was stirred well and, in the same manner as in Example 3, the percutaneous absorption type preparation of the present invention was obtained.

EXAMPLE 5

Polyisobutylene (50 parts, trademark VISTANEX MML-140, manufactured by Exxon Chemicals Japan LTD.), polyisobutylene (30 parts, HIMOL 6H, manufactured by NIPPON PETROCHEMICALS CO., LTD.) and alicyclic petroleum resin (20 parts, softening point 100° C. Arkon P-100, manufactured by ARAKAWA CHEMICAL INDUSTRIES LTD.) were dissolved in hexane to give a solution of a rubber polymer. To this solution were added tulobuterol and isopropyl myristate as an additive so that their contents in the plaster layer were 5% and 40 %, respectively. The mixture was stirred well. This solution was cast onto a release liner so that the thickness after drying became 40 μm, and dried to give a plaster layer. Then, the plaster layer was adhered to a support [laminate film of a polyester nonwoven fabric (basic weight 12 g/m$^2$) and 6 μm thick polyester film] on the nonwoven fabric side to give a percutaneous absorption type preparation of the present invention.

EXAMPLE 6

To the rubber polymer solution obtained in Example 5 were added tulobuterol and diisopropyl adipate as an additive so that their contents in the plaster layer were 5% and 30% respectively. The mixture was stirred well and, in the same manner as in Example 5, the percutaneous absorption type preparation of the present invention was obtained.

EXAMPLE 7

A styrene-butadiene-styrene block copolymer (SBS) (80 parts, styrene/butadiene=30/70 (weight ratio), trademark Cariflex TR-1101, manufactured by Shell Chemicals) and alicyclic petroleum resin (20 parts, softening point 105° C., trademark ESCOREZ 5300, manufactured by Exxon Chemicals Japan LTD.) were dissolved in toluene to give a solution of rubber polymer. To this solution were added tulobuterol and isopropyl myristate as an additive so that their contents in the plaster layer were 5% and 40%, respectively. The mixture was stirred well. In the same manner as in Example 5, the percutaneous absorption type preparation of the present invention was obtained.

EXAMPLE 8

A styrene-isoprene-styrene block copolymer (SIS) (70 parts, styrene/isoprene=14/86 (weight ratio), trademark Cariflex TR-1107, manufactured by Shell Chemicals), polyisobutylene (10 parts, trademark HIMOL 4H, manufactured by NIPPON PETROCHEMICALS CO., LTD.) and alicyclic petroleum resin (20 parts, softening point 100° C., Arkon P-100, manufactured by ARAKAWA CHEMICAL INDUSTRIES LTD.) were dissolved in toluene to give a solution of a rubber polymer. To this solution were added tulobuterol and isopropyl myristate as an additive so that their contents in the plaster layer were 5% and 40%, respectively. The mixture was stirred well. In the same manner as in Example 5, the percutaneous absorption type preparation of the present invention was obtained.

Comparative Example 1

In the same manner as in Example 1 except that an acrylic adhesive solution obtained by polymerization of tridecyl acrylate (45 parts), 2-methoxyethyl acrylate (25 parts) and vinyl acetate (30 parts) in ethyl acetate under an inert gas atmosphere was used instead of the acrylic adhesive solution used in Example 1, a percutaneous absorption type preparation was obtained.

As a result of visual or microscopic observation, the plaster layer of the preparation contained crystal dispersion of tulobuterol.

Comparative Example 2

In the same manner as in Example 5 except that a rubber polymer solution obtained by dissolving polyisoprene (70 parts, IR 2200, manufactured by Japan Synthetic Rubber Co., Ltd.) and alicyclic petroleum resin (30 parts) in hexane was used instead of the rubber polymer solution used in Example 5, a percutaneous absorption type preparation was obtained.

As a result of visual or microscopic observation, the plaster layer of the preparation contained crystal dispersion of tulobuterol.

Table 1 shows the compositions of the plaster layer of the percutaneous absorption type preparation obtained in Examples 1 to 8 and Comparative Examples 1 and 2.

TABLE 1

|  | Adhesive | Additive | Drug content | State of drug |
|---|---|---|---|---|
| Example | | | | |
| 1 | Acrylic copolymer | None | 10% | dissolved |
| 2 | Acrylic copolymer | Polyoxyethylene octylphenyl ether 10% | 10% | dissolved |
| 3 | Acrylic copolymer | Isopropyl myristate 30% | 20% | dissolved |
| 4 | Acrylic copolymer | Isopropyl myristate 40%, Glycerin monocaprylate 5% | 10% | dissolved |
| 5 | Rubber polymer (polyiso-butylene) | Isopropyl myristate 40% | 5% | dissolved |
| 6 | Rubber polymer (polyiso-butylene) | Diisopropyl adipate 30% | 5% | dissolved |
| 7 | Rubber polymer (SBS) | Isopropyl myristate 40% | 5% | dissolved |
| 8 | Rubber polymer (SIS/polyiso-butylene) | Isopropyl myristate 40% | 5% | dissolved |
| Comparative Example | | | | |
| 1 | Acrylic copolymer | none | 10% | Dispersion of crystals |
| 2 | Rubber polymer (polyisoprene) | Isopropyl myristate 40% | 5% | Dispersion of crystals |

Experimental Example 1

The percutaneous absorption type preparations obtained in Examples 1–8 and Comparative Examples 1–2, and the same percutaneous absorption type preparations after storage at 40° C. for 1 month were examined for time-course stability of adhesive property (adhesive strength).

<Adhesion Test Method>

Strip-like samples cut in 12 mm width were applied to a Bakelite board (a test plate made of phenol resin) and a roller (850 g in weight for the samples of Examples 3 and 4,300 g in weight) was reciprocated on the samples to cause close adhesion. After standing, a tensile tester (Schopper type tensile testing machine: Ueshima Seisakusho) was used to measure the adhesive strength when the strip samples were peeled off in the direction forming an angle of 180 degrees at a rate of 300 mm/min at 23° C., 60% RH.

TABLE 2

| | Adhesive strength (g/12 mm) | |
|---|---|---|
| | initial | 40° C., 1 month |
| Example | | |
| 1 | 546 | 554 |
| 2 | 413 | 408 |
| 3 | 78 | 82 |
| 4 | 66 | 63 |
| 5 | 48 | 52 |
| 6 | 58 | 55 |
| 7 | 61 | 58 |
| 8 | 64 | 60 |
| Comparative Example | | |

TABLE 2-continued

| | Adhesive strength (g/12 mm) | |
|---|---|---|
| | initial | 40° C., 1 month |
| 1 | 519 | 364 |
| 2 | 57 | 21 |

The preparations of Examples 1–8 showed stable adhesive property from the initial stage and show changes in adhesive strength with the lapse of time. In contrast, the preparations Comparative Examples 1–2 showed a decrease in adhesive strength presumably due to precipitation of drug crystals in the plaster layer with the lapse of time.

Experimental Example 2

The percutaneous absorption type preparations obtained in Examples 1, 5 and Comparative Examples 1 and 2, and the same percutaneous absorption type preparations after storage at 40° C. for 1 month were examined for time-course stability of drug release from the preparation, according to Japan Pharmacopoeia, General Test, Dissolution Test Method 2.

The results are shown Table 3.

Dissolution Test Method>

Dissolution tester: NTR-V36 (TOYAMA SANGYO CO., LTD.)

Sample size: 10 cm$^2$

Test solution: distilled water, 32° C., 500 ml

Rotation of puddle: 50 r.p.m.

Determination method: ultratraviolet absorbance method (211 nm)

TABLE 3

| | | Release percentage (%) | | | | | |
|---|---|---|---|---|---|---|---|
| | | initial | | | 40° C., 1 month | | |
| | | 3 hr | 8 hr | 24 hr | 3 hr | 8 hr | 24 hr |
| Example | 1 | 62.1 | 91.4 | 98.6 | 60.9 | 91.2 | 98.2 |
| | 5 | 47.6 | 74.7 | 93.9 | 45.8 | 75.3 | 95.1 |
| Comparative | 1 | 54.7 | 82.1 | 96.2 | 35.3 | 53.6 | 81.0 |
| Example | 2 | 39.8 | 56.4 | 82.3 | 30.1 | 45.3 | 72.2 |

The preparations of Examples 1 and 5 showed stable drug release from the initial stage and showed no changes in drug release with the lapse of time. In contrast, the preparations of Comparative Examples 1 and 2 showed a decrease in the drug release presumably due to precipitation of drug crystals in the plaster layer with the lapse of time.

Experimental Example 3

The percutaneous absorption type preparations obtained in Examples 1, 5 and Comparative Examples 1 and 2 were applied to the pre-shaved back of rabbits, and changes in tulobuterol blood concentration after the application were examined.

The results are shown in FIG. 1.

<Blood Concentration Test Method>

Sample size: 10 cm$^2$

Application site: pre-shaved back of rabbits

Application time: 24 hours

Blood concentration measurement method: gas chromatography method (electron capture ionization detector)

The preparations of Examples 1 and 5 showed excellent ascent of the blood concentration at the initial stage of the application and duration thereof. In contrast, the preparations of Comparative Examples 1 and 2 showed unsatisfactory ascent of blood concentration at the initial stage of the application, though showed superior duration thereof.

The percutaneous absorption type preparation of the present invention retains the active ingredient, tulobuterol, at a high concentration in a complete dissolution state in a plaster layer. Therefore, it is free of time-course changes in drug releasing property and adhesive property caused by precipitation of drug crystals with the lapse of time. The inventive preparation is superior in percutaneous absorption of the drug, particularly percutaneous absorption rate at the initial stage of the administration; shows superior duration of efficacy by maintaining effective blood concentration for a long time; and is associated with less changes with the lapse of time in adhesive property such as adhesion to the skin and the like.

This application is based on application Nos. 342582/1997 and 304498/1998 filed in Japan, the contents of which are incorporated hereinto by reference.

What is claimed is:

1. A percutaneous absorption preparation comprising a support and a plaster layer laminated thereon, said plaster layer comprising tulobuterol in a proportion of not less than 5 wt % in a dissolution state and an adhesive, wherein the adhesive is an acrylic adhesive or a rubber adhesive, and wherein the acrylic adhesive comprises a polymer comprising an alkyl (meth)acrylate, wherein the alkyl group has 4 to 12 carbon atoms, in a proportion of not less than 50 wt %, and wherein the rubber adhesive comprises at least one polymer selected from the group consisting of polyisobutylene and a styrene-diene-styrene block copolymer, and when the adhesive is said rubber adhesive, the plaster layer further comprises at least one additive selected from the group consisting of an ester of a fatty acid having 12 to 16 carbon atoms, monoglyceride of a fatty acid having 8 to 10 carbon atoms, an ester of a dibasic acid having 6 to 10 carbon atoms, a polyoxyethylene alkyl ether having an addition molar number of oxyethylene of 2–5, and a polyoxyethylene alkylphenyl ether having an addition molar number of oxyethylene of 2 to 5, in a proportion of 5 to 50 wt %.

2. The percutaneous absorption preparation of claim 1, wherein the acrylic adhesive comprises a copolymer comprising an alkyl(meth)acrylate, wherein the alkyl group has 4 to 12 carbon atoms, in a proportion of not less than 60 to 98 wt %, and a functional monomer having at least one unsaturated double bond in a molecule and a functional group on a side chain, in a proportion of 2 to 40 wt %.

3. The percutaneous absorption preparation of claim 2, wherein the functional group of the functional monomer is a member selected from the group consisting of carboxyl group, hydroxyl group, sulfonic acid group, amino group, amido group, alkoxyl group, cyano group and acyloxy group.

4. The percutaneous absorption preparation of claim 2, wherein the functional monomer is a member selected from the group consisting of (meth)acrylic acid, 2-hydroxyethyl (meth)acrylate, styrenesulfonic acid, (meth)acrylamide, vinyl pyrrolidone, 2-aminoethyl (meth)acrylate, acrylonitrile, 2-methoxyethyl (meth)acrylate and vinyl acetate.

5. The percutaneous absorption preparation of claim 1, wherein when the adhesive is an acrylic adhesive, the plaster layer further comprises at least one additive selected from the group consisting of an ester of a fatty acid having 12 to 16 carbon atoms, monoglyceride of a fatty acid having 8 to 10 carbon atoms, an ester of a dibasic acid having 6 to 10 carbon atoms, a polyoxyethylene alkyl ether having an addition molar number of oxyethylene of 2–5, and a polyoxyethylene alkylphenyl ether having an addition molar number of oxyethylene of 2 to 5, in a proportion of 5 to 50 wt %.

\* \* \* \* \*

UNITED STATES PATENT AND TRADEMARK OFFICE
CERTIFICATE OF CORRECTION

PATENT NO. : 6,117,447
DATED : September 12, 2000
INVENTOR(S) : Yoshihisa Nakano, Hori, Mitsuhiko, Yamamoto, Keiji, Otsuka, Saburo It is certified that error appears in the above-identified patent and that said Letters Patent is hereby corrected as shown below:

Title page,
In item "[73] Assignees", delete the hyphen ("- ") appearing between "Nitto Denko" and "Corporation".

Column 4,
Line 9, add a comma (-- , --) after "98 wt %".
Line 13, change "styrenediene-styrene" to -- styrene-diene-styrene --.

Column 5,
Line 19, change "alkyl" to -- oleyl --.

In the following locations, change "C." to -- C -- (i.e., delete the extraneous period): Column 7, lines 35 and 51; column 8, lines 10 and 27; columm 9, lines 39, 50 and 55 (in Table 2); and column 10, lines 5 (in Table 2), 22, 32 and 41 (in Table 3).

Column 9,
Line 51 (above Table 2), add the following -- The results are shown in Table 2. --

Column 10,
Line 12, change "show" to -- showed no --.
Line 26, after "shown" add -- in --.
Line 27, change "Dissolution" to -- <Dissolution --.

Signed and Sealed this

Ninth Day of October, 2001

Attest:

NICHOLAS P. GODICI
Attesting Officer
*Acting Director of the United States Patent and Trademark Office*